United States Patent [19]

Imada et al.

[11] 4,229,436

[45] Oct. 21, 1980

[54] ANTIBIOTIC G-6302

[75] Inventors: Akira Imada, Nishinomiya; Kazuaki Kitano, Sakai; Mitsuko Asai, Takatsuki, all of Japan

[73] Assignee: Takeda Chemical Industries, Ltd., Osaka, Japan

[21] Appl. No.: 971,089

[22] Filed: Dec. 15, 1978

[30] Foreign Application Priority Data

Dec. 30, 1977 [JP] Japan ................. 52/160308

[51] Int. Cl.$^3$ ............................................. A61K 35/00
[52] U.S. Cl. ..................................... 424/117; 435/170
[58] Field of Search .................. 424/117; 195/80 R; 435/170

[56] References Cited

U.S. PATENT DOCUMENTS 3,629,405 12/1971 Hamill et al. .................. 424/117

Primary Examiner—Jerome D. Goldberg
Attorney, Agent, or Firm—Wenderoth, Lind & Ponack

[57] ABSTRACT

A novel Antibiotic G-6302 is produced by cultivating a microorganism belonging to the genus Pseudomonas and being capable of producing Antibiotic G-6302 in a culture medium to have Antibiotic G-6302 elaborated and accumulated in the cultured broth and recovering the antibiotic.

Antibiotic G-6302 is useful as a germicide or disinfectant.

3 Claims, 3 Drawing Figures

Fig. 1

Fig. 2

ANTIBIOTIC G-6302

This invention relates to Antibiotic G-6302, salts thereof and a method for producing them.

For the purpose of finding new antibiotics, we isolated a large number of microorganisms from soil samples and investigated and antibiotics which such microorganisms produced. The investigation showed that some of those microorganisms would elaborate a novel antibiotic, that those microorganisms belong to the genus Pseudomonas and that, on cultivation in a suitable culture medium, those microorganisms would accumulate an antibiotic which is inhibitory to gram-positive and gram-negative bacteria. We isolated this antibiotic and, based on its physicochemical and biological properties, established that this antibiotic is a new antibiotic. We accordingly designated it Antibiotic G-6302.

The conditions for production of Antibiotic G-6302 were also studied and it was discovered that the production of Antibiotic G-6302 could be significantly increased by growing any of those microorganisms in a culture medium supplemented with a sulfur compound which the microorganism is able to utilize. These findings were followed by further research which culminated in the present invention.

Throughout this specification and the claims forming parts of this application, Antibiotic G-6302 will sometimes be referred to briefly as G-6302.

This invention is therefore directed to:
(1) Antibiotic G-6302 and salts thereof; and (2) A method for production Antibiotic G-6302 characterized by cultivating a microorganism which belongs to the genus Pseudomonas and is capable of producing Antibiotic G-6302 in a culture medium to have Antibiotic G-6302 elaborated and accumulated in the cultured broth and recovering the antibiotic.

The Antibiotic G-6302-producing strain employed in accordance with this invention may be any bacterial strain of the genus Pseudomonas only if it is able to elaborate Antibiotic G-6302. As an example of such strain, there may be mentioned Pseudomonas Strain G-6302 (hereinafter referred to sometimes as Strain G-6302) which we isolated from soil samples collected in Ashigara-Shimo-Gun, Kanagawa Prefecture, Japan.

The bacteriological characteristics of Pseudomonas Strain G-6302 are as follows.

(a) Morphology:

After 2 days on a nutrient-agar slant at 28° C., the cells are rod-shaped, 0.7 to 1.0μ in diameter and 0.7 to 3.5μ long. Without polymorphism, motile with polar flagella or a polar flagellum. Non-sporulating; no accumulation of poly-beta-hydroxybutyric acid as an intracellular carbon reserve (R. Y. Stanier et al: Journal of General Microbiology 43, 159 (1966)). Gram-negative, nonacid-fast.

(b) Cultural characteristics on various media:

Grown at 28° C. and observed for 1 to 14 days.

(1) Nutrient agar plate: Circular, raised colonies of 1 to 3 mm diameter with entire margins are formed after 3 days; smooth; opaque; white; no diffusible pigment produced.

(2) Nutrient agar slant: Moderate growth, filiform, opaque and cream-colored.

(3) Nutrient broth: Turbid growth, substantially without sedimentation. A pellicle appears after 14 days of cultivation.

(4) Nutrient gelatin stab: Surface growth, without liquefaction.

(5) Litmus milk: No change (c) Physiological characteristics
(1) Reduction of nitrates: Negative
(2) Denitrification: Negative
(3) MR (methyl red) test: Negative
(4) VP (Voges-Proskauer) test: Negative
(5) Production of indole: Negative
(6) Production of hydrogen sulfide: Positive (weak)
(7) Hydrolysis of starch: Negative
(8) Utilization of citrate: Positive
(9) Utilization of inorganic nitrogen sources
(I) Potassium nitrate: Negative to weakly positive
(II) Ammonium sulfate: Positive
(10) Production of pigments: None
(11) Urease: Positive
(12) Oxidase: Negative
(13) Catalase: Positive
(14) Range of growth
(I) pH: Growth at pH 4 to 8, optimal pH 4.5–6.0
(II) Temperature: Growth at 2° to 37° C., optimal 25° to 30° C.
(15) Oxygen demand: Aerobic
(16) O-F (oxidative-fermentative) test (Hugh-Leifson method): Oxidative
(17) Production of acid and gas from sugars: Weak acid production but no gas production is noted in peptone-water containing 1 W/V % of D-glucose, D-mannose, D-galactose, maltose, sucrose, trehalose, D-sorbitol, D-mannitol, inositol or glycerol.
(18) Assimilation of carbon sources:

The results of cultivation in inorganic salt media (dipotassium hydrogen phosphate 0.7 W/V%, monopotassium dihydrogen phosphate 0.3 W/V%, ammonium sulfate 0.1 W/V%, sodium chloride 0.1 W/V%, magnesium sulfate. 7$H_2O$ 0.01 W/V%) containing various carbon sources for 14 days are given in Table 1.

TABLE 1

Assimilation of Carbon Sources

| Carbon source | Final concentration (W/V %) | Growth |
|---|---|---|
| L-Arabinose | 1 | + |
| D-Xylose | 1 | + |
| D-Glucose | 1 | + |
| D-Mannose | 1 | + |
| D-Fructose | 1 | + |
| D-Galactose | 1 | + |
| Maltose | 1 | + |
| Sucrose | 1 | + |
| Lactose | 1 | − |
| Trehalose | 1 | + |
| D-Sorbitol | 1 | + |
| D-Mannitol | 1 | + |
| Inositol | 1 | + |
| Glycerol | 1 | + |
| Starch | 1 | − |
| α-Methyl-D-glucoside | 1 | + |
| Melibiose | 1 | − |
| Adonitol | 1 | + |
| Dulcitol | 1 | − |
| Raffinose | 1 | + |
| cis-Aconitate | 0.3 | + |
| Citrate | 0.3 | + |
| Isocitrate | 0.3 | + |
| Gluconate | 0.3 | + |
| Acetate | 0.3 | + |
| Fumarate | 0.3 | + |
| Malate | 0.3 | + |
| Tartarate | 0.3 | + |
| p-Hydroxybenzoate | 0.3 | + |
| L-Alanine | 0.3 | + |

TABLE 1-continued

| Assimilation of Carbon Sources | | |
|---|---|---|
| Carbon source | Final concentration (W/V %) | Growth |
| β-Alanine | 0.3 | + |
| L-Isoleucine | 0.3 | + |
| Succinate | 0.3 | + |
| L-Valine | 0.3 | − |
| 2-Ketogluconate | 0.3 | + |

Notes:
+: Growth
±: Scant growth
−: No growth (19) Other properties
 (I) Utilization of malonate: Negative
 (II) Deamination of phenylalanine: Negative
 (III) Decarboxylase activity
  (a) Arginine: Negative
  (b) Lysine: Negative
  (c) Ornithine: Negative
 (IV) Hydrolysis of esculin: Positive
 (V) Hydrolysis of Tween 80: Positive
 (VI) The GC (guanine-cytosine) content of DNA: 59.5 mol %

Comparison of the above bacteriological characteristics of Strain G-6302 with the description in Bergey's Manual of Determinative Bacteriology, Ed. 7 & 8, shows that, in view of its being a gram-negative rod-shaped bacterium, strictly aerobic, motile with a polar flagellum or flagella and catalase-positive, Strain G-6302 obviously belongs to the family Pseudomonadaceae. The fact that it has no nutritional requirements and has a GC content of 59.5 mol % suggests that the strain belongs to the genus Pseudomonas. As Pseudomonas bacteria is relatively akin to Strain G-6302 in respect of the above characteristics, there may be mentioned *Pseudomonas syringae* and *Pseudomonas maltophilia*, which are cytochrome oxidase negative. *P. maltophilia*, however, is evidently different from Strain G-6302 in that *P. maltophilia* is methionine-demanding and gives no growth at 4° C. While *Pseudomonas syringae* is a species including a large number of nomenspecies, it is clear from Table 2 that the inability to utilize certain carbon sources as a common trait of such strains is not found in Strain G-6302.

TABLE 2

| Comparison of Assimilability of Various Carbon Sources | | |
|---|---|---|
| Carbon source | *Pseudomonas syringae* | Strain G-6302 |
| Trehalose | − | + |
| 2-Ketogluconate | − | + |
| β-Alanine | − | + |
| L-Isoleucine | − | + |

+: assimilated
−: not assimilated

Moreover, the optimal pH for growth of Strain G-6302 is very low, viz 4.5 to 6.0, growth occurring even at pH 4.0. These differences eliminate the possibility of regarding Strain G-6302 as a strain of *Pseudomonas syringae*. Therefore, G-6302 is considered to belong to a new species of the genus Pseudomonas. And in view of the feature that its low optimal growth pH is 4.5 to 6.0, which is low for bacteria of the genus Pseudomonas generally, Strain G-6302 was named *Pseudomonas acidophila* G-6302.

Samples of this Strain G-6302 have been respectively deposited at the Fermentation Research Institute, Agency of Industrial Science and Technology (FERM), Chiba, Japan under deposit number of FERM-P No. 4344, at Institute for Fermentation, Osaka (IFO), Japan under the accession number of IFO 13774 and at the American Type Culture Collection, (ATCC), Maryland, U.S.A. under the accession number of ATCC-31363.

The Pseudomonas bacteria employed in accordance with this invention generally are highly variable in characteristics and undergo mutation readily when subjected to artificial mutagenic treatments such as irradiation with ultraviolet light or X-rays or treatment with chemical mutagens. However, any and all of such mutants and variants are useful for the purposes of this invention only if they possess and retain the ability to elaborate G-6302, the subject antibiotic of this invention.

For the cultivation of Strain G-6302, there may be employed such carbon sources as glucose, sucrose, maltose, spent molasses, gylcerol, oils and fats (e.g. soybean oil, olive oil, etc.), organic acids (e.g. citric acid, succinic acid, gluconic acid, etc.) and other assimilable carbon sources. As nitrogen sources there may be employed organic and inorganic nitrogen-containing compounds and materials such as, for example, soybean flour, cottonseed flour, corn steep liquor, dried yeast, yeast extract, meat extract, peptone, urea, ammmonium sulfate, ammonium nitrate, ammonium chloride, ammonium phosphate, etc. Moreover, the inorganic salts normally required for cultivation of bacteria, such as sodium chloride, potassium chloride, calcium carbonate, magnesium sulfate, monopotassium dihydrogen phosphate, disodium monohydrogen phosphate, etc., may be employed either alone or in a suitable combination. It has been found that the yield of the desired antibiotic can be increased by supplementing such a medium with a sulfur compound which the G-6302 producer is able to utilize, viz. inorganic sulfur compounds such as sulfates (e.g. sodium sulfate), thiosulfates (e.g. sodium thiosulfate), etc. or organic sulfur compounds such as sulfur-containing amino acids (e.g. cystine, cysteine, methionine), etc. For this purpose, sodium thiosulfate is particularly preferred. The concentration of such sulfur compounds in the culture medium is 0.01 to 1.0 W/V percent and, preferably, 0.02 to 0.5 W/V percent. Addition of such a sulfur compound to the medium results in an increased production of G-6302 thus being commercially of considerable value.

In addition, salts of heavy metals such as ferrous sulfate, copper sulfate, etc., vitamins such as vitamin $B_1$, biotin, etc. and other additives may be incorporated as required. Antifoams and surfactants such as silicone oil, polyalkylene glycol ether, etc. may also be added. Of course, other organic or inorganic matters which would assist in growth of the microorganism and promote production of G-6302 may also be added in suitable amounts.

The cultivation of Strain G-6302 may be conducted by procedures similar to those used for the production of antibiotics in general, employing a solid culture or a liquid culture method. In the case of liquid culture, it may be stationary, stirring, shaking or aerobic, although aerobic stirring culture is particularly desirable. The preferred cultivation temperature range is about 15° to 35° C., while the pH of the culture medium may range from about 4 to 8. The cultivation is continued for about 8 to 168 hours, preferably for 24 to 144 hours. Since the product Antibiotic G-6302 is for the most part present in the liquid phase of the fermentation broth, it is advantageous to centrifuge or filter the broth to separate supernatant fluid or filtrate from a cellular mass and purify G-6302 in the supernatant fluid or filtrate. However, direct purification from the fermentation broth is also feasible, if desired.

Assay of the potency of the product thus obtained may be performed against *Proteus mirabilis* IFO 3849 as the test organism and using G-6302 as the standard by the cylinder method or paper disk method employing TSA [trypticase soy agar (Baltimore Biologicals, Laboratories, U.S.A.)].

Antibiotic G-6302 may be recovered by means of the various procedures commonly employed for the recovery of microbial metabolites. Thus, for example, the cells are removed by centrifugation and the active product is separated from the supernatant fluid and purified by the conventional methods. For example, the procedure which makes use of the solubility or solubility difference with respect to a suitable solvent, the procedure utilizing the precipitation or difference in the rate of precipitation of the antibiotic from a solution, the procedure which utilizes its characteristic adsorptive affinity for various adsorbents, ion exchange chromatography on ion-exchangers, concentration under reduced pressure, freeze-drying, crystallization, recrystallization, drying, etc. may be utilized either singly or in a suitable combination and sequence or/and in repetition.

A typical procedure may be described below. Thus, after the cultivation has been completed, the fermentation broth is filtered, the resultant filtrate is passed through a column of activated charcoal and the adsorbed G-6302 is eluted with a hydrophilic organic solvent. As examples of the hydrophilic organic solvent there may be mentioned lower ketones (e.g. acetone, methyl ethyl ketone, methyl isobutyl ketone, etc.), lower alcohols (e.g. methanol, ethanol, isopropanol, propanol, butanol, etc.). These solvents may be used alone or as a mixture in combination with water. Because of the acidic nature of the G-6302, anion exchange resins such as Cl-form resins [Amberlite IRA-400 & 402, manufactured by Amberlite Co., U.S.A.; Dowex-1, Dow and Chemical Co., U.S.A.; Diaion SA-21A, Mitsubishi Chemical Industries, Japan] can be employed with advantage. The adsorbed active product is eluted, for example with an aqueous solution of sodium chloride. To desalt the eluate, column chromatography is carried out again with activated charcoal. The eluate obtained is then concentrated, acetone, for instance, is added and the resultant precipitate is recovered by filtration, washed with acetone, diethyl ether and dried under reduced pressure to recover light-brown powders. To purify G-6302 in the powders, column chromatography on DEAE-Sephadex (Pharmacia, Sweden) can be employed with advantage. Thus, a column of DEAE-Sephadex A-25 is washed with M/100 phosphate buffer (pH 6.6) and an aqueous solution of the above powders is passed through the column and the antibiotic is adsorbed thereon. The column is washed with the same buffer solution as above and elution is carried out with the buffer containing 0.5 W/V% of sodium chloride. The active fractions are pooled, adjusted to pH 3.0 and passed again through a column of activated charcoal. The column is washed with water and 20 V/V% aqueous methanol successively. Elution is then carried out with aqueous acetone and the active fractions are pooled and concentrated under reduced pressure. Acetone is added to the concentrate, whereby G-6302 is obtained. G-6302 forms metal salts and ammonium salt. As the metal salts there may be mentioned the sodium salt, potassium salt, lithium salt, etc.

The physico-chemical properties of the G-6302 obtained in Example 1 which appears hereinafter are as follows.

1. Melting point: 120° C. (sintering), 130° C. (decomp.)
2. Appearance: White powders
3. Elemental analysis: (after drying under reduced pressure over phosphorus pentoxide at 40° C. for 6 hours)(%): C 34.83, 35.45 (34.99±0.5); H 5.41, 5.24 (5.58±0.5); N 13.22, 13.73 (13.60±0.5); S 7.65, 7.75 (7.70±0.5); O (38.13±0.5).
4. Molecular weight:
   Titrometry: 400±20
   Empirical formula (based on the above data) $C_{12}H_{20}N_4SO_9 \cdot H_2O$ Calc. C, 34.78; H, 5.35; N, 13.52; S, 7.74
5. Ultraviolet absorption spectrum:
   End absorptions only (no characteristic absorptions over 210 nm)
6. Infrared absorption spectrum (FIG. 1), dominant peaks (KBr) (cm$^{-1}$):
   3440(s), 2920(m), 2850(m), 2600(w), 1770(s), 1650(s), 1530(s), 1458(m), 1390(w), 1340(w), 1280(sh), 1240(s), 1210(sh), 1180(m), 1118(w), 1043(s), 792(w), 632(s) (s, m and w mean strong, medium and weak absorptions, respectively; sh means shoulder.)
7. Specific rotation: $[\alpha 23_D + 94° \pm 10°(c=0.35, H_2O)$
8. Nuclear magnetic resonance spectrum (in dimethylsulfoxide, 100 MHz) δ3.31 ppm(s, a chemical shift assignable to O-CH$_3$)
9. Solubility in solvents:
   Insoluble in petroleum ether, hexane, diethyl ether, benzene, ethyl acetate and chloroform; sparingly soluble in ethanol, pyridine and acetone; soluble in methanol and dimethylsulfoxide; readily soluble in water.
10. Color reactions:
    Positive:ninhydrin and potassium permanganate reactions; negative:ferric chloride-potassium ferricyanide, Sakaguchi and Molisch reactions; doubtful positive: Ehrlich reaction.
11. Stability:
    Stable in aqueous solution in the range of pH 3-pH 7 at 60° C. for 10 minutes; unstable over pH 8.5.
12. Basicity, neutrality or acidity: Acid.

The physico-chemical properties of the sodium salt of G-6302 obtained in Example 3 which appears hereinafter are as follows.

1. Melting point: No definite melting point (browning at 170° C.)
2. Appearance: White powders
3. Elemental analysis (after drying under reduced pressure and over phosphorus pentoxide at 40° C. for 6 hours) (%):
   C 33.08, 33.32;
   H 5.07, 4.97;
   N 12.73, 13.27;
   S 7.33, 7.43;
   Na 5.19, 5.31.
4. Molecular weight: 438±5, assuming that 1 mol of Na is contained by each molecule.
   Empirical formula (based on the above data) $C_{12}H_{19}N_4SO_9Na \cdot H_2O$
   Calc. C, 33.03; H, 4.85; N, 12.84; S, 7.35; Na, 5.27

5. Ultraviolet absorption spectrum: End absorptions only.
6. Infrared absorption spectrum (FIG. 2), dominant peaks (KBr) (cm$^{-1}$):
3430(s), 3250(sh), 3000(m), 1770(s), 1640(s), 1530(s), 1450(w), 1405(w), 1343(w), 1280(sh), 1245(s), 1180(w), 1118(w), 1050(s), 820(w), 785(w), 632(s) (s, m and w mean strong, medium and weak absorptions, respectively; sh means shoulder.)
7. Specific rotation: $[\alpha]_D^{23} \pm 85° \pm 10°(c=0.37, H_2O)$
8. Solubility in solvents: Insoluble in petroleum ether, hexane, diethyl ether, benzene, ethyl acetate, chloroform and acetone; sparingly soluble in methanol, ethanol and pyridine; soluble in dimethylsulfoxide; readily soluble in water.
9. Color reactions: Positive: ninhydrin and potassium permanganate reactions; negative: ferric chloride-potassium ferricyanide, Sakaguchi and Molisch reactions; doubtful positive: Ehrlich reaction
10. Stability:

Stable in aqueous solution in the range of pH 3–pH 7 at 60° C. for 10 minute heating; unstable over pH 8.5.

To convert the free acid form of G-6302 to a salt, the sodium salt, for instance, can be obtained by adding a molar equivalent of sodium hydroxide to an aqueous solution of the free acid and then freeze-drying the system.

To convert a salt of G-6302 to the free acid form, the latter can be obtained, for example by adding 1 N-hydrochloric acid to an aqueous solution of the sodium salt, for instance, of G-6302 to bring the solution to pH 3.0 and desalting the solution by means of activated charcoal.

The biological characteristics of G-6302 are as follows. The antimicrobial spectra of G-6302 and its sodium salt against various microorganisms are shown in Table 3 (agar plate dilution method.)

It will be apparent from this table that Antibiotic G-6302 is mainly active against gram-negative bacteria but is also active against some gram-positive bacteria.

The acute toxicity of the sodium salt of Antibiotic G-6302 is low, with no deaths being encountered when 500 mg/kg of the salt was administered to mice by the intravenous route.

G-6302 was also found to have a protecting action on mice infected with Escherichia coli or Klebsiella pneumoniae at the subcutaneous dose of 10 mg/kg or at the oral dose of 100 mg/kg.

TABLE 3

Antimicrobial Spectra of G-6302 and its Sodium Salt

| Test organism | Minimal inhibitory concentration(mcg/ml) | |
|---|---|---|
| | G-6302 | G-6302 . Na |
| Escherichia coli NIHJ | 25 | 25 |
| Escherichia coli T-7 | 25 | 25 |
| Salmonella typhosa Boxhill 58 | 12.5 | 12.5 |
| Shigella flexneri EW-10 | 25 | 25 |
| Klebsiella pneumoniae DT | 12.5 | 12.5 |
| Proteus vulgaris IFO 3988 | 100 | 100 |
| Proteus morganii IFO 3168 | 100 | 100 |
| Proteus mirabilis IFO 3849 | 25 | 25 |
| Serratia marcescens IFO 12648 | 100 | 100 |
| Pseudomonas aeruginosa U-31 | >100 | >100 |
| Staphylococcus aureus FDA 209P | >100 | >100 |
| Streptococcus pyogenes E-14 | >100 | >100 |
| Bacillus subtilis PCI 219 | 100 | 100 |
| Corynebacterium diphtheriae Toronto | 12.5 | 12.5 |
| Candida albicans IFO 0583 | >100* | >100* |
| Saccharomyces cerevisiae IFO 0209 | >100* | >100* |
| Aspergillus niger IFO 4066 | >100* | >100* |
| Penicillium chrysogenum IFO 4626 | >100* | >100* |

Notes:
Medium = Trypticase-soy-broth-agar
*Medium = Nutrient agar containing 1% of glucose As will be seen from the above antimicrobial spectrum, G-6302 according to this invention is inhibitory to gram-negative and gram-positive bacteria. Therefore, it can be used in the treatment of infections with the above-mentioned bacteria in mammalian animals (e.g. mouse, rat, dog and man) and domesticated avian species (e.g. fowl and duck). To use G-6302 as a remedy of Escherichia coli infections, it is dissolved in physiological saline, for instance, and parenterally administered, e.g. subcutaneously or intramuscularly, at the dose level of 5 to 30 mg/kg body weight daily. For oral use, Antibiotic G-6302 is admixed with lactose, for instance, encapsulated and administered at the dose level of 20 to 200 mg (as G-6302)/kg body weight daily.

G-6302 may also be used as a germicide or disinfectant. For instance, G-6302 is dissolved in distilled water to prepare a solution containing 0.1 to 1.0 W/V percent of G-6302 or formulated with an ointment basis such as vaseline or lanolin to prepare an ointment containing 5 to 20 mg of G-6302 per gram and said solution or ointment is applied to the paws, legs, eyes, ears or other parts of the above-mentioned animals as a disinfectant.

G-6302 is a very promising compound in that it is useful as an intermediate for the synthesis of new medical substances.

Comparison of Antibiotic G-6302 with the known antibiotics has revealed the following. First, as antibiotics which are soluble in water and acidic and contain sulfur, there may be mentioned penicillins and cephalosporins. However, in that G-6302 does not absorb in the ultraviolet region of the spectrum, it differentiates itself from cephalosporins. Moreover, the fact that the nuclear magnetic resonance spectrum gives a chemical shift assignable to O-methyl protons and the fact that it gives rise to glutamic acid on acid hydrolysis are the lines of evidence that G-6302 is different from any of the naturally occurring penicillins and cephalosporins.

On the other hand, there are many known antibiotics elaborated by bacteria of the genus Pseudomonas but none of them is a water-soluble antibiotic which is acidic and contains sulfur. Moreover, G-6302 is dissimilar to any of the known antibiotics produced by microorganisms other then Pseudomonas strains in view of its unique physicochemical and biological properties. Therefore, G-6302 is considered to be a new compound.

The following examples are further illustrative of this invention.

In the examples, "part(s)" is based on weight unless otherwise noted and the relationship between "part(s)" and "part(s) by volume" corresponds to that between "gram(s)" and "milliliter(s)" and "%" is based on "weight/volume" unless otherwise noted.

EXAMPLE 1

The cells of *Pseudomonas acidophila* G-6302 (FERM-P No. 4344; IFO 13774; ATCC-31363) grown on a nutrient agar slant were used to inoculate two $2 \times 10^3$ parts by volume Sakaguchi flasks each containing 500 parts by volume of a medium composed of 1% glucose, 0.5% Polypepton (prepared by Daigo Nutritive Chemicals Co. Japan), 0.5% meat extract 0.5% sodium chloride (pH 7.0) and each flask was incubated on a reciprocating shaker at 28° C. for 48 hours. The resultant culture was used as a seed culture.

A $200 \times 10^3$ parts by volume stainless steel tank fermentor was filled with $120 \times 10^3$ parts by volume of a medium composed of 3% glycerol, 0.1% glucose, 0.5% Polypepton, 0.5% meat extract and 0.5% NaCl and, after adjustment to pH 7.0 with 30% aqueous sodium hydroxide, sterilized with steam at 120° C. for 20 minutes. The sterilized tank was then inoculated with the above seed culture and incubated at a temperature of 28° C. with aeration at the rate of $120 \times 10^3$ parts by volume/min. and at 180 r.p.m. agitation for 78 hours. The resultant broth was centrifuged with a Sharples centrifugal separator to remove the cells, which left $110 \times 10^3$ parts by volume of supernatant fluid. The fluid was adjusted to pH 4.2 and passed through a column of $15 \times 10^3$ parts by volume of activated charcoal (chromatographic Grade SHIRASAGI, manufactured by Takeda Chemical Industries, Ltd., Japan) to have active substance adsorbed thereon. The column was rinsed with $45 \times 10^3$ parts by volume of water and, then, elution was carried out with $45 \times 10^3$ parts by volume of 50 V/V% aqueous acetone, the eluate being collected in $10 \times 10^3$ parts by volume fractions. The fractions were assayed against *Proteus mirabilis* IFO 3849. The fractions Nos. 2 and 3 were pooled, $20 \times 10^3$ parts by volume of water was added and the mixture was passed through a column packed with $10 \times 10^3$ parts by volume of Dowex-1 (Cl-form) (Dow and Chemical Industries, U.S.A.). The column was rinsed with $25 \times 10^3$ parts by volume of water and elution was carried out with $50 \times 10^3$ parts by volume of a 5% aqueous sodium chloride solution. The active fractions were pooled, adjusted to pH 4.0 and passed again through a column of activated charcoal ($8 \times 10^3$ parts by volume). The column was washed with $24 \times 10^3$ parts by volume of water and elution was carried out with 20 V/V% aqueous methanol. The active fractions were pooled and concentrated to 50 parts by volume under reduced pressure. Then, 200 parts by volume of acetone was added and the resultant precipitate was recovered by filtration, washed with 50 parts by volume of acetone and 100 parts by volume of diethyl ether, followed by drying under reduced pressure. By the above procedure there was obtained 12 parts of crude product.

Figure 1:
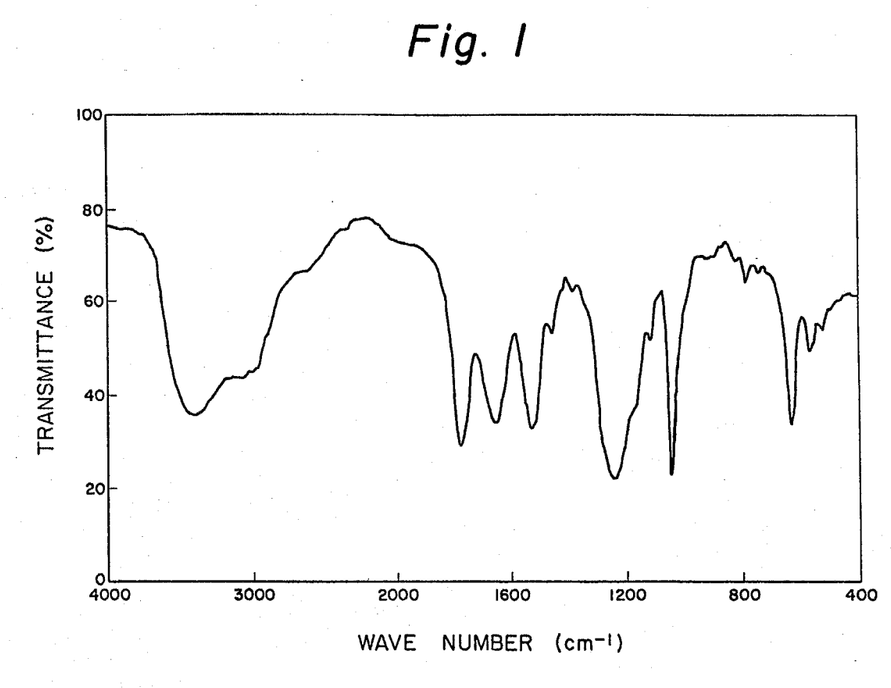

In 500 parts by volume of M/100 phosphate buffer (pH 6.6) was dissolved 10 parts of the above crude product and the solution was passed through a column of 200 parts by volume of DEAE-Sephadex A-25 (Pharmacia, Sweden) previously buffered with the same buffer solution as mentioned. The column was washed with 400 parts by volume of the same buffer solution and, then, elution was carried out with the same buffer to which 0.5% of sodium chloride had been added. The active fractions were pooled, adjusted to pH 3.2 with 1 N-HCl and passed through a column of 60 parts by volume of activated charcoal. The column was washed with 200 parts by volume of water and 100 parts by volume of 20 V/V% aqueous methanol, followed by eluting with 50 V/V% aqueous acetone. The active fractions were pooled, concentrated under reduced pressure and dissolved in 5 parts by volume of methanol. Following addition of 100 parts by volume of acetone, the solution was allowed to stand in the cold. The resultant precipitate was recovered by filtration, washed with diethyl ether and dried under reduced pressure and over phosphorus pentoxide at 40° C. for 6 hours. By the above procedure there was obtained 3.8 parts of powder. The infrared absorption spectrum of this product is shown in FIG. 1.

Elemental analysis: C 34.83; H 5.41; N, 13.22; S, 7.65 (W/W%)

EXAMPLE 2

A $50 \times 10^3$ parts by volume stainless steel tank fermentor was filled with $35 \times 10^3$ parts by volume of a medium composed of 3% glycerol, 0.1% glucose, 0.5% Polypepton, 0.5% meat extract and 0.5% sodium chloride and, after the medium was adjusted to pH 7.0 with 30% aqueous sodium hydroxide, sterilized with steam at 120° C. for 20 minutes. The sterilized tank was inoculated with the same strain of microorganism as that used in Example 1 and incubated at 28° C. with aeration at the rate of $35 \times 10^3$ parts by volume/min. and at 180 r.p.m. agitation for 48 hours to prepare a secondary seed culture.

A $2000 \times 10^3$ parts by volume stainless steel tank fermentor was filled with $1200 \times 10^3$ parts by volume of a medium composed of 3% glycerol, 0.1% glucose, 0.5% Polypepton, 0.5% meat extract, 0.5% sodium chloride and 0.1% sodium thiosulfate and, after adjustment to pH 7.0 with a 30% solution of sodium hydroxide, sterilized with steam at 120° C. for 20 minutes. The sterilized tank was inoculated with the above secondary seed culture.

The inoculated tank medium was incubated at 28° C. with aeration at the rate of $1200 \times 10^3$ parts by volume/min. and at 180 r.p.m. agitation for 90 hours, whereby $1150 \times 10^3$ parts by volume of broth was obtained. To this broth was added $40 \times 10^3$ parts of Hyflo-Supr-Cel (Johnes-Manville, U.S.A.) and filtered with a filter press. The filtrate was adjusted to pH 4.2 with 4 N-sulfuric acid and passed columnwise over $120 \times 10^3$ parts by volume of activated charcoal. The column was washed with $300 \times 10^3$ parts by volume of water and elution was carried out with 50 V/V% aqueous acetone. The active fractions were pooled and concentrated under reduced pressure to remove the acetone. The aqueous concentrate thus obtained was diluted with water to $200 \times 10^3$ parts by volume and passed through a column of $50 \times 10^3$ parts by volume of Diaion SA-21A (Cl-form) (manufactured by Mitsubishi Chemical Industries, Japan). The column was rinsed with $150 \times 10^3$ parts by volume of water and elution was carried out with 1% aqueous sodium chloride. The active fractions were pooled and concentrated under reduced pressure to 100 parts by volume, then $2 \times 10^3$ parts by volume of methanol was added and the precipitated sodium chloride was filtered off. The filtrate was further concentrated under reduced pressure to 200 parts by volume, then $2 \times 10^3$ parts by volume of acetone was added and the precipitate was recovered by filtration and dried. By the above procedure there was obtained 757 parts of crude product. This crude product (500 parts) was dissolved in $5 \times 10^3$ parts by volume of water, adjusted to pH 4.0 and adsorbed on a column of activated charcoal ($5 \times 10^3$ parts by volume). The active ingredient was eluted by the gradient elution method using $10 \times 10^3$ parts by volume of water through $10 \times 10^3$ parts by volume of 70 V/V% aqueous methanol and the eluate was collected in $1 \times 10^3$ parts by volume fractions. The active fractions were pooled, concentrated under reduced pressure to remove the methanol and made up to $6 \times 10^3$ parts by volume with M/100 phosphate buffer (pH 6.0). This sample solution was adsorbed on a column of $3 \times 10^3$ parts by volume of DEAE-Sephadex A-25 which had been prepared as described in Example 1 and, after the column was washed with $6 \times 10^3$ parts by volume of the same buffer, elution was carried out with the same buffer supplemented with 0.5% of sodium chloride, the eluate being collected in 500 parts by volume fractions. The active fraction were pooled, adjusted to pH 3 with 1 N-HCl and passed through a column of $0.5 \times 10^3$ parts by volume of activated charcoal. The column was washed with $2 \times 10^3$ parts by volume of water through $2 \times 10^3$ parts by volume of 20 V/V% aqueous methanol and, then, elution was carried out with 50 V/V% aqueous acetone, the eluate being collected in 200 parts by volume fractions. The active fractions were pooled, concentrated under reduced pressure and dissolved by addition of 300 parts by volume of methanol. Following addition of $3 \times 10^3$ parts by volume of acetone and $4 \times 10^3$ parts by volume of diethyl ether, the solution was allowed to stand in the cold and the precipitated G-6302 was recovered by filtration, washed with diethyl ether and dried under reduced pressure and over phosphorus pentoxide. Yield 72 parts.

Elemental analysis: C, 35.45; H, 5.24; N, 13.73; S, 7.75 (W/W%).

EXAMPLE 3

Figure 2:
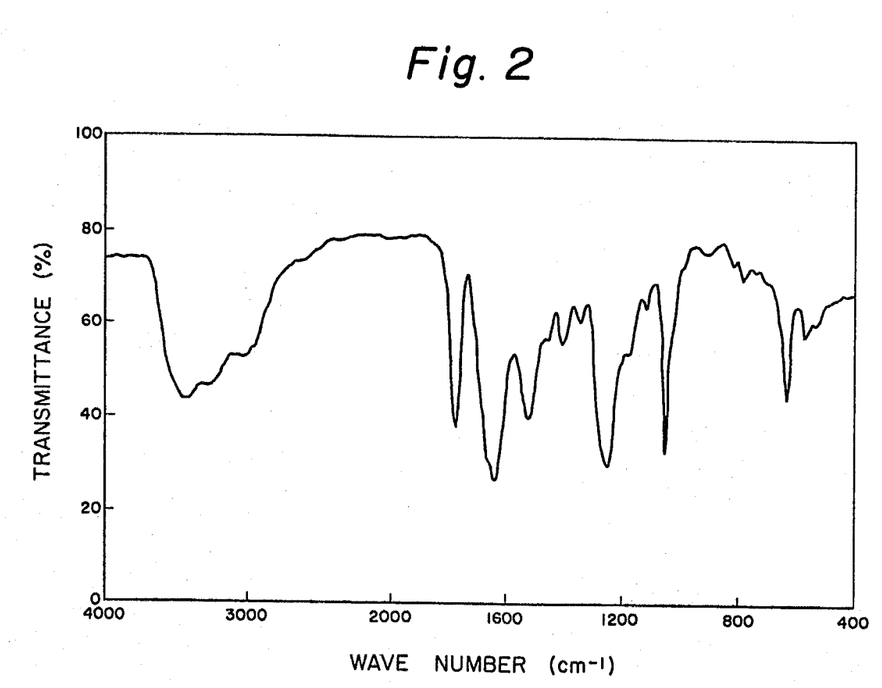

In 90 parts by volume of water was dissolved 4.0 parts of the free form of G-6302 obtained in Examples 1 and 2, and under cooling, about 9.0 parts by volume of 1 N-aqueous sodium hydroxide was added. This was followed by the addition of a further amount of 1 N-sodium hydroxide with the pH of the solution being monitored until the pH of 6.5 was established. The solution was freeze-dried, whereby 4.2 parts of G-6302 monosodium salt was obtained as white powders. The infrared absorption spectrum of this product after drying under reduced pressure and at 40° C. for 6 hours is shown in FIG. 2.

Elemental analysis: C, 33.08; H, 5.07; N, 12.73; S, 7.33, Na 5.19 (W/W%).

EXAMPLE 4

The cells of *Pseudomonas acidophila* G-6302 (FERM-P No. 4344; IFO 13774; ATCC-31363) grown on a nutrient agar slant were used to inoculate a 200 parts by volume conical flask containing 40 parts by volume of a medium composed of 1% glucose, 0.5% Polypeption, 0.5% meat extract and 0.5% sodium chloride (pH 7.0) and the inoculated flask was incubated on a rotary shaker at 28° C. for 48 hours to prepare a seed culture.

Then, 200 parts by volume conical flasks were each filled with 40 parts by volume of a medium composed of 3% glycerol, 1% glucose, 0.5% Polypepton (Daigo Nutritive Chemicals), 0.5% meat extract and 0.5% sodium chloride (pH 7.0), and 0.02 to 0.5% of various sulfur compounds were added to the flasks. Each flask was then inoculated with 1 part by volume of the above seed culture and incubated on a rotary shaker at 28° C. for 96 hours. As will be apparent from the following table, the production of G-6302 was markedly increased by the addition of sulfur compounds.

| Sulfur compound | Concentration (%) | Production (μg/ml) |
|---|---|---|
| Not added | — | 15 |
| Methionine | 0.02 | 20 |
| | 0.5 | 43 |
| Cysteine | 0.02 | 55 |
| | 0.1 | 65 |
| Cystine | 0.02 | 30 |
| | 0.5 | 65 |
| Sodium sulfate | 0.02 | 70 |
| | 0.1 | 48 |
| Sodium thiosulfate | 0.02 | 55 |
| | 0.1 | 80 |

EXAMPLE 5

In 7.5 parts by volume of cold water was dissolved 1 part of the free form of G-6302 obtained in Examples 1 or 2, and to the mixture was added 17.5 parts by volume of cold methanol.

Thus obtained mixture was kept standing in the cold for 24 hrs. to have powders of G-6302 crystallized into colorless crystals. The crystals were recovered, washed with a small amount of 80 V/V% cold aqueous methanol, cold methanol and ether successively and dried over phosphorus pentoxide under reduced pressure at 60° C. for 6 hours, whereby 0.930 part of crystals of G-6302 was obtained. The physico-chemical properties of thus obtained crystals are as follows:

1. Melting point: 168° to 170° C.
2. Elemental analysis: (W/W%) Found; C 35.51 35.56; H 5.61 5.61; N 12.93 12.98; S 7.45 7.59.

Calculated as $C_{12}H_{20}N_4SO_9 \cdot CH_3OH \cdot \frac{1}{2}H_2O$; C 35.69; H 5.76; N 12.81; S 7.33.

Figure 3:
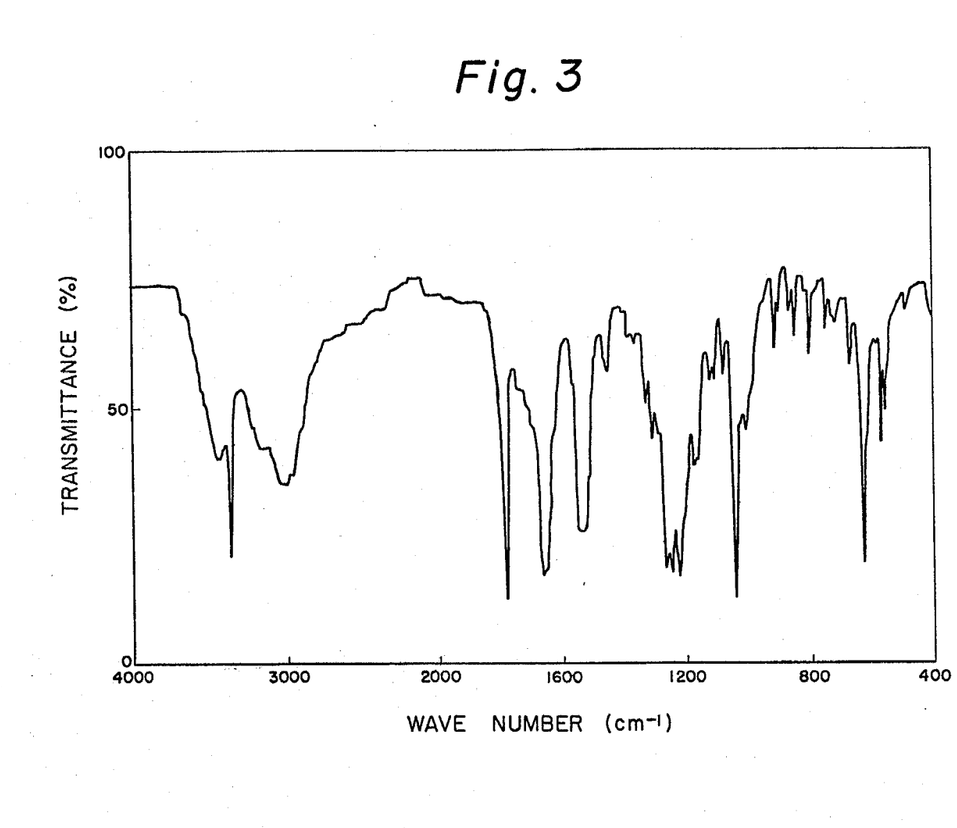

3. Specific rotation: $[\alpha]_D^{23} + 82° \pm 5°$ (c=1.0, in $H_2O$)
4. Infrared absorption spectrum (FIG. 3), dominant peaks (KBr) (cm$^{-1}$):
3440, 3355, 3000, 1780, 1660, 1650, 1538, 1265, 1245, 1220, 1038, 625
5. Nuclear magnetic resonance spectrum: in dimethylsulfoxide, 100 MHz)

$\delta 3.31$ ppm (s, 3H) (a chemical shift assignable to O-$CH_3$ of G-6302)

$\delta 3.20$ ppm (s, 3H) (a chemical shift assignable to O-$CH_3$ of methanol which is contained in the crystals.

Other physico-chemical properties, i.e. ultraviolet absorption spectrum, solubility in solvents, color reactions, stability and basicity, neutrality or acidity, are the same as those of the product obtained in Example 1.

What we claim is:

1. A member selected from the group consisting of Antibiotic G-6302 having the following characteristics, and a metal or ammonium salt thereof:
   (1) Melting point: 120° C. (sintering), 130° C. (decomp.)
   (2) Appearance: white powder
   (3) Elemental analysis: (%) C 34.99, ±0.5; H 5.58, ±0.5; N 13.30, ±0.5; O 38.13, ±0.5; S 7.70, ±0.5 (as dried at 40° C. for 6 hours over phosphorus pentoxide under reduced pressure)
   (4) Ultraviolet absorption spectrum: No characteristic absorptions over 210 nm
   (5) Infrared absorption spectrum [KBr, dominant absorptions (wave-numbers, cm$^{-1}$)]: 1770, 1650, 1530, 1240, 1043

(6) Specific rotation: $[\alpha]_D^{23} +94°\pm 10°$ (c=0.35, $H_2O$)

(7) Solubility: Insoluble in petroleum ether, hexane, diethyl ether, benzene, ethyl acetate and chloroform; sparingly soluble in ethanol, pyridine and acetone; soluble in methanol and dimethylsulfoxide; and readily soluble in water (8) Basicity, neutrality or acidity: Acid (9) Molecular weight: 400±20 (by titrometry)

(10) Color reactions: Positive: ninhydrin and potassium permanganate reactions; negative: ferric chloride-potassium ferricyanate, Sakaguchi and Molisch reactions; doubtful positive: Ehrlich reaction.

2. A method for producing Antibiotic G-6302 as defined in claim 1 comprising cultivating a microorganism having the characteristics of *Pseudomonas acidophila* G-6302 (ATCC 31363) in a culture medium containing an assimilable carbon source and a digestible nitrogen source under aerobic conditions at pH 4 to 8 and at a temperature of the range of 15° to 35° C. until Antibiotic G-6302 is substantially elaborated and accumulated in the cultured broth and recovering Antibiotic G-6302 therefrom.

3. A method as claimed in claim 2, wherein the culture medium is supplemented with 0.01 to 1.0 w/v% of a sulfur compound which is assimilated by the microorganism and which is selected from the group consisting of sodium thiosulfate, sodium sulfate, cystine, cysteine and methionine.

* * * * *